US005717181A

United States Patent [19]

Colgate

[11] Patent Number: 5,717,181

[45] Date of Patent: Feb. 10, 1998

[54] METHOD OF REDUCING CONCENTRATION OF HIGH MOLECULAR WEIGHT COMPONENT IN MIXTURE OF COMPONENTS

[75] Inventor: Samuel O. Colgate, Gainesville, Fla.

[73] Assignee: University of Florida, Gainesville, Fla.

[21] Appl. No.: 644,948

[22] Filed: May 13, 1996

[51] Int. Cl.$^6$ .............................. C07C 1/00; C07C 2/00; C07C 4/00; B01D 17/06

[52] U.S. Cl. .............................. 204/157.15; 204/157.42; 204/158.2; 210/748

[58] Field of Search ......................... 204/157.15, 157.42, 204/158.2; 210/748

[56] References Cited

U.S. PATENT DOCUMENTS

| | | | |
|---|---|---|---|
| 3,457,108 | 7/1969 | Hittel | 134/22 |
| 4,120,699 | 10/1978 | Kennedy, Jr. et al. | 134/1 |
| 4,193,635 | 3/1980 | Thiruvengadam et al. | 299/17 |
| 4,328,865 | 5/1982 | Hall | 166/302 |
| 4,697,426 | 10/1987 | Knowles, Jr. | 62/48 |
| 4,702,758 | 10/1987 | Geer | 62/532 |
| 5,254,177 | 10/1993 | Chauvin | 134/8 |
| 5,289,838 | 3/1994 | Odell | 134/166 |
| 5,547,563 | 8/1996 | Stowe | 208/106 |

FOREIGN PATENT DOCUMENTS 702811 1/1954 United Kingdom .

*Primary Examiner*—Kathryn L. Gorgos
*Assistant Examiner*—Edna Wong
*Attorney, Agent, or Firm*—Kerkam, Stowell, Kondracki & Clarke; Dennis P. Clarke

[57] ABSTRACT

A method of reducing the concentration of, e.g., wax, in a liquid admixture with, e.g., crude oil, comprising subjecting the liquid to cavitation such that temperatures, pressures and shear forces are produced in the liquid sufficient to induce cracking of the wax, but insufficient to induce significant decomposition of lower molecular weight components of the crude oil and continuing the method for a time sufficient to lower the concentration of the wax in the crude oil.

6 Claims, 2 Drawing Sheets

METHOD OF REDUCING CONCENTRATION OF HIGH MOLECULAR WEIGHT COMPONENT IN MIXTURE OF COMPONENTS

BACKGROUND OF THE INVENTION

1. Field of the Invention

The present invention relates to methods for reducing the concentration of higher molecular weight, labile organic components in mixtures thereof with lower molecular weight, less labile organic components with particular emphasis on reducing the concentration of waxy components in crude oil while undergoing transport in pipelines or conduits from subsea and land based reservoirs to the surface, thereby preventing deposition of wax on the interior pipeline surfaces.

2. Description of the Prior Art

Crude oils are complex mixtures of chemical species, mainly of hydrocarbon molecules. Reservoir fluids with significant concentrations of heavy hydrocarbons (waxes) often tend to separate into two phases (liquid, solid) during production. This presents problems when the wax drops out and deposits on surfaces which are difficult to reach for periodic service. An important example is the inside of conduits bringing crude oil from subsea reservoirs to the surface. The dropout of wax and the concomitant restriction of effective pipe size or even plugging of the line are favored by the cooling and reduction in pressure which the fluid experiences as its rises toward the sea surface. A suitable means of preventing such wax deposition, especially during this phase of production, is greatly needed.

To date, most efforts have been directed toward periodic removal of the deposits from the conduit or pipe interior surfaces after deposition; a costly and inefficient process. Wax removal by pigging is probably the most commonly employed method.

U.S. Pat. No. 3,457,108 describes one such method which comprises removing adhering materials from a surface part of a vessel, such as deposits from tube walls of closed vessels, by urging liquid treating agent into or through the vessel while subjecting the treating agent to cyclic stress to induce cavitations at a repetition rate of between one time per minute and five hundred times per minute. The treating agent may include various chemical cleaning agents, usually in dilute solutions. This method is said to be superior to the so-called "fill and soak" method wherein the vessel (or tube) to be cleaned is pumped full of the treating liquid and then soaked for a predetermined time while the treating liquid loosens or dissolves the adhering material. Alternatively, the treating liquid is continuously flowed through the vessel or tube to achieve the above-stated desired result.

U.S. Pat. No. 4,328,865 relates to a system for controlling wax formation in oil wells using a thermal syphon wherein a confined annular space between the production tube and the oil stream casing is provided by means of a plug or "packer" installed at a point well below the level at which solid waxes begin to deposit out of the exiting crude oil, and a plug or "packer" installed above the point at which waxes would otherwise stop depositing out of the exiting crude oil and thereafter filling the confined annulus with a fluid working medium. The quantity and properties of the fluid working medium are arranged such that the medium is vaporized at the lower extremities of the confined annulus and condensed on the surfaces of the upper regions of the confined annulus, particularly in the zone of wax deposition. The condensation process warms the production tube sufficiently to prevent formation of adhesive wax deposits or, alternatively, re-liquifies a thin film of deposited wax which enables the flowing crude oil to remove the deposited wax. The condensed working medium flows by gravity to the lower part of the confined annulus where it again becomes available for vaporization and subsequent condensation. However, this method would only be effective in situations where the appropriate temperature differential is inherent in the system. Moreover, the method requires the introduction into the system of a separate fluid which must be maintained separate from the production stream. It appears to be a "bootstrap" method. Heat is drawn from the flowing liquid in a region of high temperature and returned thereto at a region of lower temperature. No external heat is added and, therefore, no net gain in solution stability is realized.

U.S. Pat. Nos. 4,697,426 and 4,702,758 describe a method for cooling oil quickly to below its cloud point without any wax deposition. The oil and natural gas stream preferably is cooled by conventional means to slightly above the cloud point. The oil and gas are then cooled to below the cloud point with an isenthalpic pressure drop through a choke. The wax comes out of solution as the oil is cooled. The wax does not deposit in the choke or downstream of the choke as the wax precipitates in the bulk stream and not at the wall. Such a system would be effective only in a restricted range of applications. It would not, for example, be employed in transporting oil from subsea reservoirs to the sea surface via pipeline since the "bulk stream" is not amenable to treatment since it is located below the bottom of the sea. Moreover, this system changes the morphology of wax crystals and, therefore, the kinetics of plate out. It does not change the thermodynamic driving force to produce wax.

U.S. Pat. Nos. 4,120,699; 4,193,635 and 5,289,838 disclose methods for removing deposits from the interior walls of conduits, tubes or pipes by ultrasonic generation of cavitation in liquids therein which loosen the deposits.

There is needed in the art an inexpensive and efficient method for preventing the formation of solid waxy deposits in the interior surfaces of pipelines and conduits conveying crude oil, particularly from subsea reservoirs to sea surfaces.

It is an object of the present invention to provide a system useful, e.g., for lowering in a mixture the concentration of a high molecular weight component, thereby reducing its tendency to deposit out of a liquid which is not subject to the above-noted disadvantages.

SUMMARY OF THE INVENTION

The above and other objects are realized by the present invention, one embodiment of which relates to a method of reducing the concentration of at least one higher molecular weight organic component (HMWC) in a liquid comprising the at least one HMWC in admixture with at least one lower molecular weight organic component (LMWC), the at least one HMWC being distinguishable from the at least one LMWC by the presence therein of at least one chemical bond which is more labile than the chemical bonds present in the at least one LMWC; the method comprising subjecting the liquid to cavitation such that temperatures and pressures are produced in the liquid sufficient to induce cracking of the at least one labile chemical bond in the at least one HMWC, but insufficient to induce significant decomposition of the at least one LMWC, and continuing the method for a time sufficient to lower the concentration in the liquid of the at least one HMWC and concomitantly raising the concentration in the liquid of the at least one LMWC.

DESCRIPTION OF PREFERRED EMBODIMENTS

Figure 1:
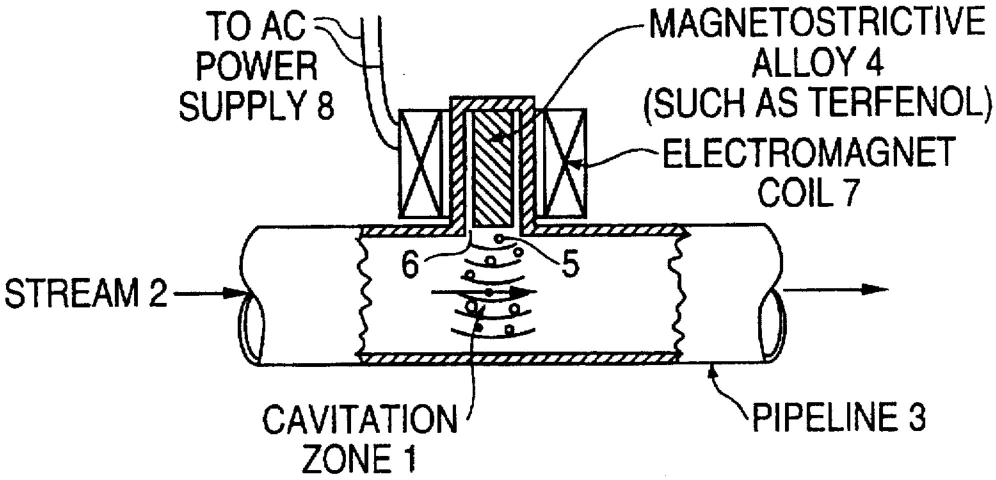
FIGS. 1, 2 and 2A are sectioned elevational views of an active system for carrying out an embodiment of the method of the invention.

A preferred embodiment of the invention relates to an improved method for conveying crude oil from a subsea reservoir to the sea surface in a conduit wherein crude oil undergoes cooling as a result of a reduction in pressure and by heat flow to the surrounding area as the crude oil rises toward the sea surface; the improvement comprising a method for raising the cloud point of the crude oil in the conduit, thereby reducing the deposition of heavy hydrocarbon waxes from the crude oil onto the interior surfaces of the conduit, the method comprising subjecting the crude oil in the conduit at a region in the conduit wherein the crude oil is below the cloud point, i.e., at or near the sea floor to cavitation such that temperature and pressures are produced in the crude oil sufficient to induce cracking of the heavy hydrocarbon waxes, but insufficient to induce significant decomposition of non-wax components of the crude oil.

Another embodiment of the invention comprises applying the same method to underground crude oil reservoirs.

The present invention is predicated on the discovery that labile higher molecular weight organic components (HMWC) may be cracked in liquid admixture thereof with less labile, lower molecular weight organic components (LMWC) to produce lower molecular weight fractions of the HMWC's and thereby reduce the concentration thereof in liquid mixture without significantly affecting the LMWC's in the mixture by subjecting the mixture to cavitation under conditions such that localized regions of the high temperatures and pressures and shear and pressure shock required for such cracking reactions to occur are produced in the liquid mixture.

For the purpose of facilitating the description of the invention herein, the terms and phrases listed hereinbelow have the following meanings and/or definitions.

"Higher Molecular Weight Component" (HMWC) refers to any organic compound of relatively high molecular weight containing at least one labile chemical bond which is subject to cracking to produce lower molecular weight fractions of the HMWC at certain conditions of temperature and pressure.

"Lower Molecular Weight Component" (LMWC) refers to organic compounds having a molecular weight lower than that of the HMWC's and characterized by the absence therein of labile chemical bonds which are subject to cracking at the conditions of temperatures and pressure which induce cracking of the HMWC's.

"Labile" refers to chemical bonds in HMWC's subject to cracking at elevated temperatures, pressures and shear forces to produce lower molecular weight fractions of the HMWC.

"Cavitation" refers to the formation of partial vacuums in a liquid by high-intensity sound waves or by the movement of the liquid past solid reactive surfaces; the term "reactive" referring to any solid surface which induces non-linear behavior in the moving liquid such that localized conditions of elevated temperatures and pressures are produced in the liquid.

"Crude oil" denotes petroleum oil as produced from the ground or any fluid derived from such oil.

"Wax" refers to any substance contained in crude oil, for example, paraffin or the like or asphaltenes and the like which have a relatively low temperature of crystallization or cloud point.

"Cloud point" refers to the temperature at which waxes crystallize out as solids or semi-solids in crude oil and tend to deposit on walls of, for example, conduits in which the crude oil is being conveyed.

Although the method of the invention is particularly applicable to the inhibition of wax deposits on the interior surfaces of conduits conveying crude oil, it will be apparent to those skilled in the art that the method of the invention may be employed to reduce the concentration of the HMWC's in any liquid admixture thereof with LMWC's. A particular advantage of the method of the invention resides in the fact that it results in the conversion of undesirable HMWC's such as waxes in crude oils to more valuable LMWC's therein, eliminating or reducing the cost of subsequent removal of the undesirable HMWC's (waxes).

Examples of liquid mixtures of HMWC's and LMWC's other than crude oil to which the method of the invention is applicable include (1) animal or vegetable oils or fats in which lower molecular weight molecules with more unsaturated bonds are more suitable for use as ingredients and in preparation of foods; and (2) waste water streams contaminated with HMWC's. Sonication in aqueous solution produces active radicals which promote many useful secondary reactions, including decomposition of halogenated molecules such as PCB's, and refrigerants, amino acids and benzenes. The HMWC may be a bacterium or other biological cell which is destroyed by the process.

The method of the invention is most efficient when applied to liquids in a state of flow in conduits or pipes, e.g., the flow of crude oil in conduits from subsea reservoirs to the sea surface.

Cavitation in the liquid mixtures of LMWC's and HMWC's to induce cracking in and a reduction of the concentration of the latter may be achieved according to the method of the invention according to either of two strategies or embodiments.

The first embodiment comprises an active strategy, i.e., subjecting the liquid to high intensity sound waves, e.g., ultrasonic waves, which produce localized regions of elevated temperatures, pressures and shear forces high enough to induce chemical bond breaking or cracking in the HMWC's, thereby lowering the concentration thereof while increasing the concentration of LMWC's. In a preferred embodiment of this strategy, ultrasonic transducers are coupled to a flowing stream and electrically driven to induce cavitation in the liquid. In a complex mixture such as crude oil, the labile bonds of the largest molecules (i.e., the waxes) will be most affected, i.e., cracked to produce small molecular fragments.

A second strategy involves a passive means for accomplishing the same result. As the breaking of chemical bonds is necessarily an endoergic process, some supply of energy is required to decrease the HMWC concentration by cracking. Rather than supply the energy externally as in the first embodiment described above, it is possible to tap into the considerable energy available in a flowing stream. Liquids flowing past reactive surfaces exhibit non-linear behavior including separation and cavitation. Fluid handling equipment and machinery are usually designed to eliminate or minimize these effects, which tend to lower efficiency. In this embodiment of the method of the invention, a section of the flow line is deliberately fitted with structures to enhance cavitation and promote HMWC molecule cracking. Other modes of inducing cavitation in liquid mixtures of HMWC's and LMWC's will be apparent to those skilled in the art.

The method of the invention will be described in detail in the examples hereinbelow with reference to the drawings, wherein identical components or features are marked with identical reference numerals.

EXAMPLE 1

Referring to FIG. 1, a cavitation zone 1 is induced in a stream of crude oil 2 in pipeline 3 by a magnetostrictive alloy 4, e.g., terfenol. One end 5 of the alloy is exposed to the flowing stream through an opening 6 in the pipeline. The alloy is excited to oscillate dimensionally by an AC electric current 8 in a wound coil 7 deployed external of the pipeline. The frequency of oscillation is selected to match a natural frequency of the alloy such that an efficient transmission of acoustic energy to the cavitation zone is achieved. The frequency and power are sufficiently high to produce cavitation in zone 1 in the passing crude oil stream. Only one transducer is depicted in FIG. 1; however, it will be apparent to those skilled in the art that an array of multiple transducers can be deployed around the pipeline to influence a greater percentage of the HMWC's or wax molecules flowing therethrough.

EXAMPLE 2

Figure 2:
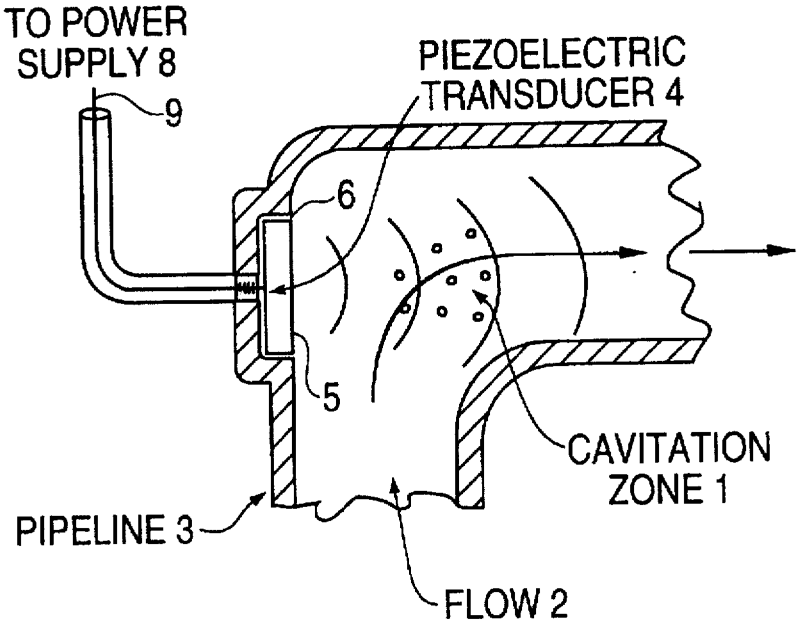
Figure 2A:
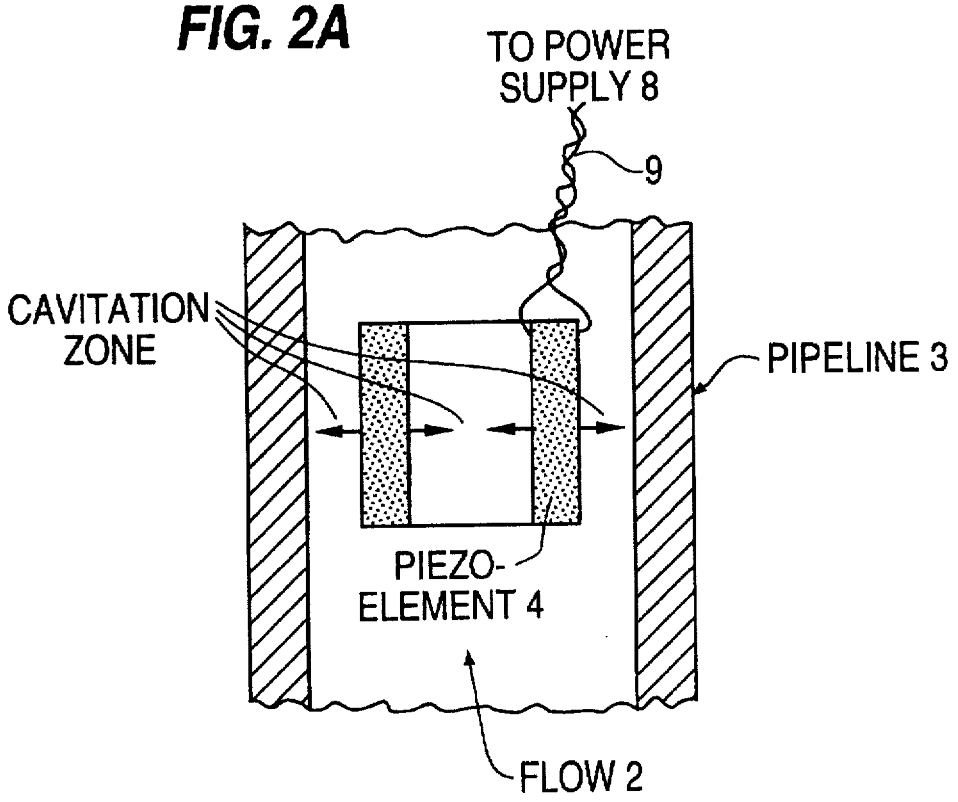

Referring to FIG. 2, a similar system is shown wherein a piezoelectric element or transducer 4 such as a quartz crystal or piezoceramic material is employed as the active member. In this case, it is necessary to penetrate the conduit wall with the power leads 9. Driving the piezo element with an AC voltage at the natural frequency of the element causes acoustic waves at that frequency to be propagated into the fluid stream. Alternatively, as shown in FIG. 2A, the piezo element 4 may be lowered into the well string and operated by power delivered through a feed cable 9. The piezo element undergoes dimensional oscillations depending on the material and its crystalline or polling characteristics. In this arrangement, the element is a cylinder deployed downhole, concentric with the pipeline and operated so as to radiate ultrasonic pressure waves radially. Cavitation occurs inside the cylinder bore and in the annulus between its outer wall and the pipe I.D. These may be gauged in multiple stages as needed to produce sufficient cracking of the HMWC's to prevent wax deposition upstream.

EXAMPLE 3

Figure 3:
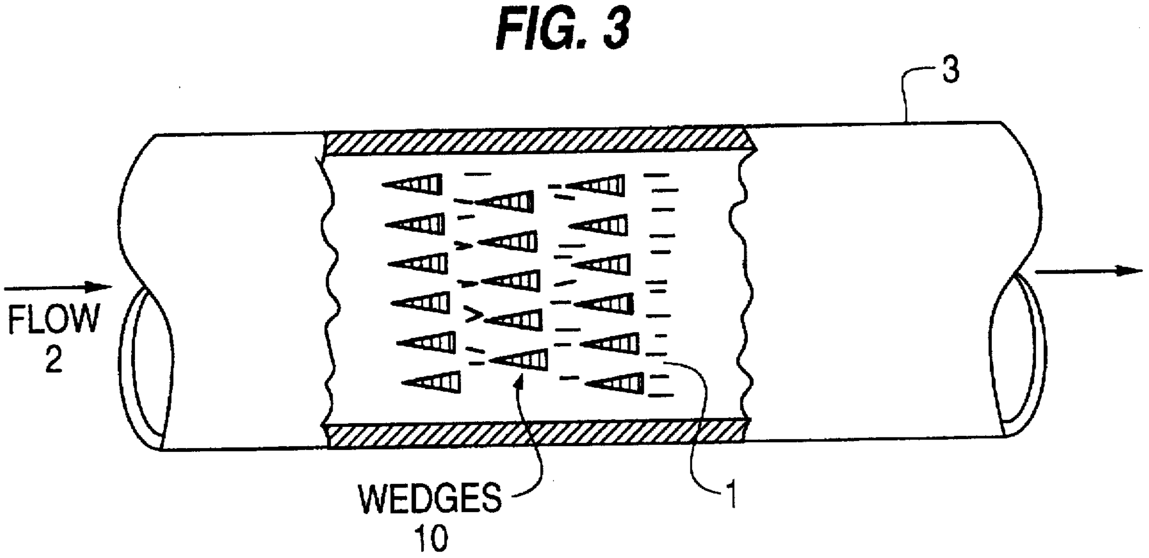
FIG. 3 is a sectioned elevational view of a passive system for carrying out an embodiment of the method of the invention.

Referring to FIG. 3, a passive device is shown comprising an array of reactive surfaces 10 in the pipeline 3 which intercept the flow momentarily. Cavitation will occur in the downstream fluid in zone 1. This effect may, of course, be multiplied by using a system of cascaded struts. The figure shows a simple wedge geometry which is known to be capable of producing cavitation, but it will be obvious that other geometries may be used and the spacings adjusted as needed to maximize the desired effects; that is, to lower the driving force for wax dropout without unduly slowing production at the surface. If the wedges are configured as vibrating reeds, supported at their nodal points, the impinging fluid will set them into vibration. Such devices are known as "liquid whistles" and are useful for inducing cavitation.

I claim:

1. In a method of conveying crude oil from a sub-sea or underground crude oil reservoir to the surface in a conduit wherein said crude oil undergoes cooling as a result of (1) a reduction in pressure as said crude oil rises toward the surface, (2) heat transfer, or (3) both (1) and (2), the improvement consisting of a method for raising the cloud point of said crude oil in said conduit, such that deposition of heavy hydrocarbon waxes from said crude oil onto interior surfaces of said conduit is reduced, said method consisting of subjecting said crude oil in said conduit at or near the sub-sea or underground reservoir to cavitation wherein temperatures and pressures are produced in said crude oil sufficient to induce cracking of said heavy hydrocarbon waxes, but insufficient to induce significant decomposition of non-wax components of said crude oil.

2. The method of claim 1 wherein said cavitation is induced by subjecting said crude oil to high intensity sound waves.

3. The method of claim 1 wherein said cavitation is induced by providing reactive surfaces within said conduit wherein said crude oil thereover induces non-linear cavitation therein.

4. A method of reducing deposition of waxes in conduits conveying crude oil consisting essentially of subjecting said crude oil during said conveyance to cavitation wherein temperatures and pressures are produced in said crude oil sufficient to induce cracking of said waxes, but insufficient to induce significant decomposition of non-wax components of said crude oil.

5. The method of claim 4 wherein said cavitation is induced by subjecting said crude oil to high intensity sound waves.

6. The method of claim 4 wherein said cavitation is induced by flowing said crude oil across reactive surfaces which induce non-linear behavior of said flowing crude oil amounting to said cavitation.

* * * * *